United States Patent [19]

Nichols et al.

[11] Patent Number: 4,603,700

[45] Date of Patent: Aug. 5, 1986

[54] PROBE MONITORING SYSTEM FOR OXIMETER

[75] Inventors: Robert A. Nichols; David R. Tobler, both of Thornton, Colo.

[73] Assignee: The BOC Group, Inc., Montvale, N.J.

[21] Appl. No.: 559,734

[22] Filed: Dec. 9, 1983

[51] Int. Cl.$^4$ ............................................. G01N 33/16
[52] U.S. Cl. ..................... 128/633; 128/653; 128/665; 356/41; 364/416
[58] Field of Search ................................. 128/632-634, 128/653, 654, 663-667; 356/39-42; 364/416, 417

[56] References Cited

U.S. PATENT DOCUMENTS 3,591,290  7/1971  Zinner et al. .................. 128/633
3,638,640  2/1972  Shaw .............................. 128/633
3,647,299  3/1972  Lavallee ......................... 128/633
4,407,290  10/1983  Wilber ............................ 128/633

Primary Examiner—John F. Niebling
Assistant Examiner—Terryence Chapman
Attorney, Agent, or Firm—Roger M. Rathbun; Larry R. Cassett

[57] ABSTRACT

A monitor system for an oximeter that sequentially tests the operative conditions of light emitting devices of the oximeter, the light detector of the oximeter, and the reference voltage of the oximeter. Data processing means is responsive to the determined test values for indicating the occurrence of the test values outside of predetermined ranges corresponding to the respective test value.

9 Claims, 7 Drawing Figures

FIG. 2C  FIG. 2D
FIG. 2B
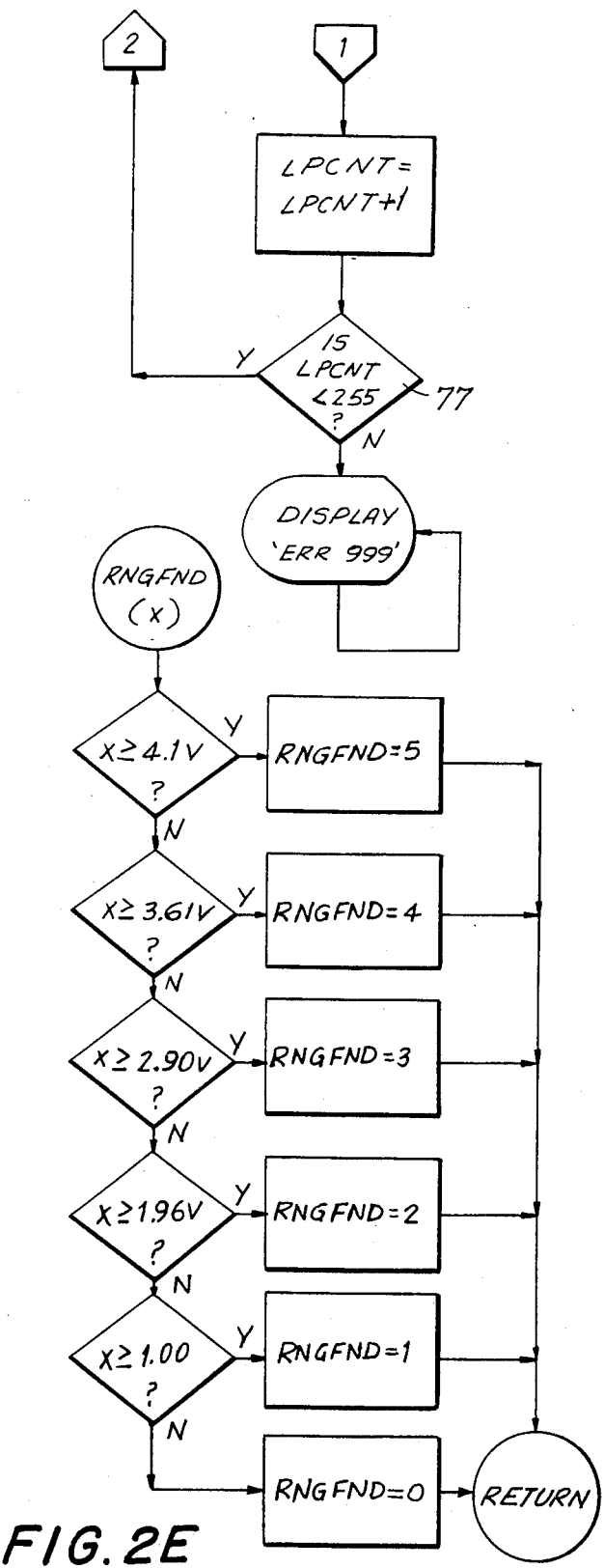
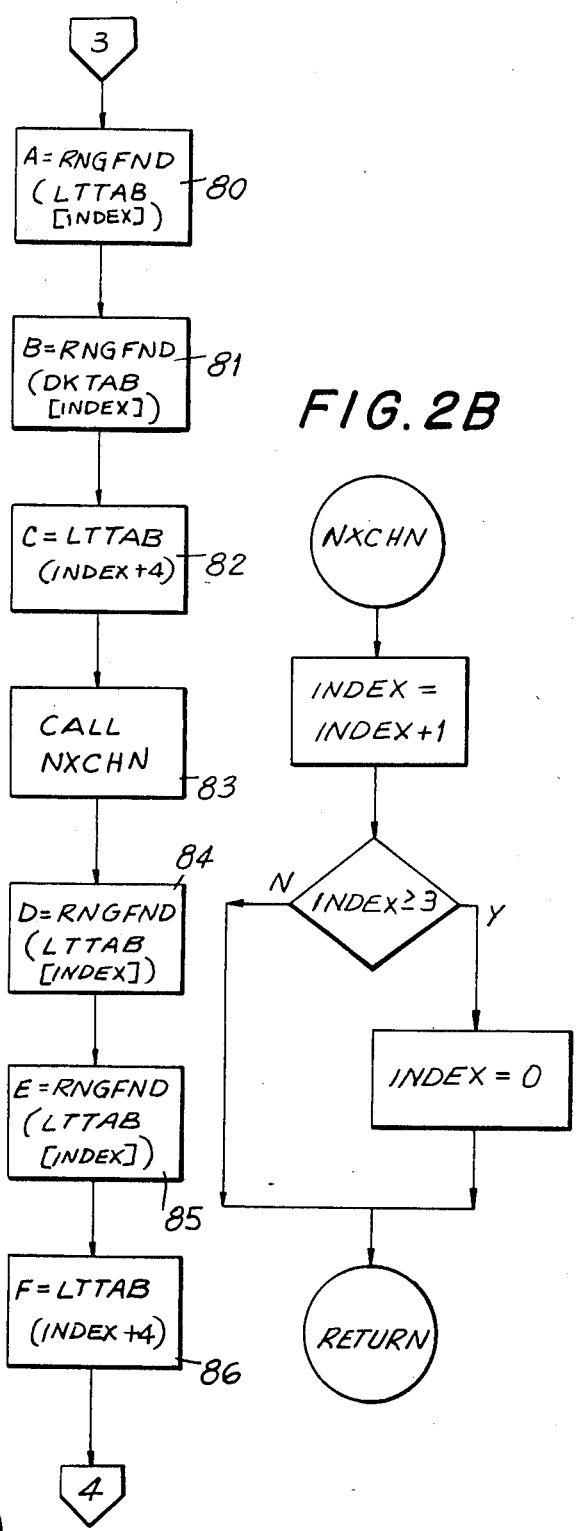
FIG. 2E

PROBE MONITORING SYSTEM FOR OXIMETER

This invention relates to a probe monitoring system for an oximeter, and is particularly to the provision of a monitoring apparatus enabling the automatic determination of proper operating conditions in an oximeter.

An oximeter of the type to which the present invention is concern is a non-invasive blood constituent measuring device disclosed, for example, in U.S. Pat. No. 4,407,290, Scott A. Wilber, assign to Biox Technology Inc., of Boulder, Colo. In a non-invasive oximeter of this type, a plurality of light emitting diodes emitting light at different wavelengths are directed toward a blood-containing tissue. The diodes are sequentially energized by a timing circuit. A photodiode receives light from the tissue, the output from the photodiode being normalized with respect to a standard voltage, and processed in a pair of channels responsive to light of the two different wavelengths respectively. The resultant signals, corresponding to aborption by the blood of energy at the two wavelengths, are processed in a microprocessor, in accordance with a given algorithm, in order to ascertain the various constituents of the blood, such as oxygen.

The present invention is directed to the provision of a measuring system for continuously determining the operability of various critical elements of an oximeter of the above type, such as the light emitting diodes and photodetector, as well as a reference voltage used by the oximeter for normalizing the signals.

Briefly stated, in accordance with the invention, voltages derived from the light emitting diode circuits and photodetector circuits, reference and voltage source are time multiplexed and applied to an analog to digital converter. The output of the analog to digital converter is applied to a microprocessor programmed to provide suitable output messages corresponding to the conditions of operation of these elements.

BRIEF DESCRIPTION OF THE DRAWINGS

In order that the invention will be more clearly understood it will now be disclosed in greater detail with reference to the accompanying drawing, wherein:

FIGS. 2A, 2B, 2C, 2D, 2E and 2F illustrate a flow diagram of the monitoring system of the ionvention.

Referring now to FIG. 1, therein is illustrated an oximeter of the type disclosed in U.S. Pat. No. 4,407,290, in simplified form, and modified to incorporate the monitoring system of the invention. The elements of the illustrated system, incorporating the oximeter, which are disclosed in greater detail in U.S. Pat. No. 4,407,290, will first be briefly described, in order to enable a fuller understanding of the functioning of the monitor system of the invention. The disclosure of U.S. Pat. No. 4,407,290 is hence incorporated by reference herein.

BRIEF DESCRIPTION OF THE OXIMETER

Figure 1:
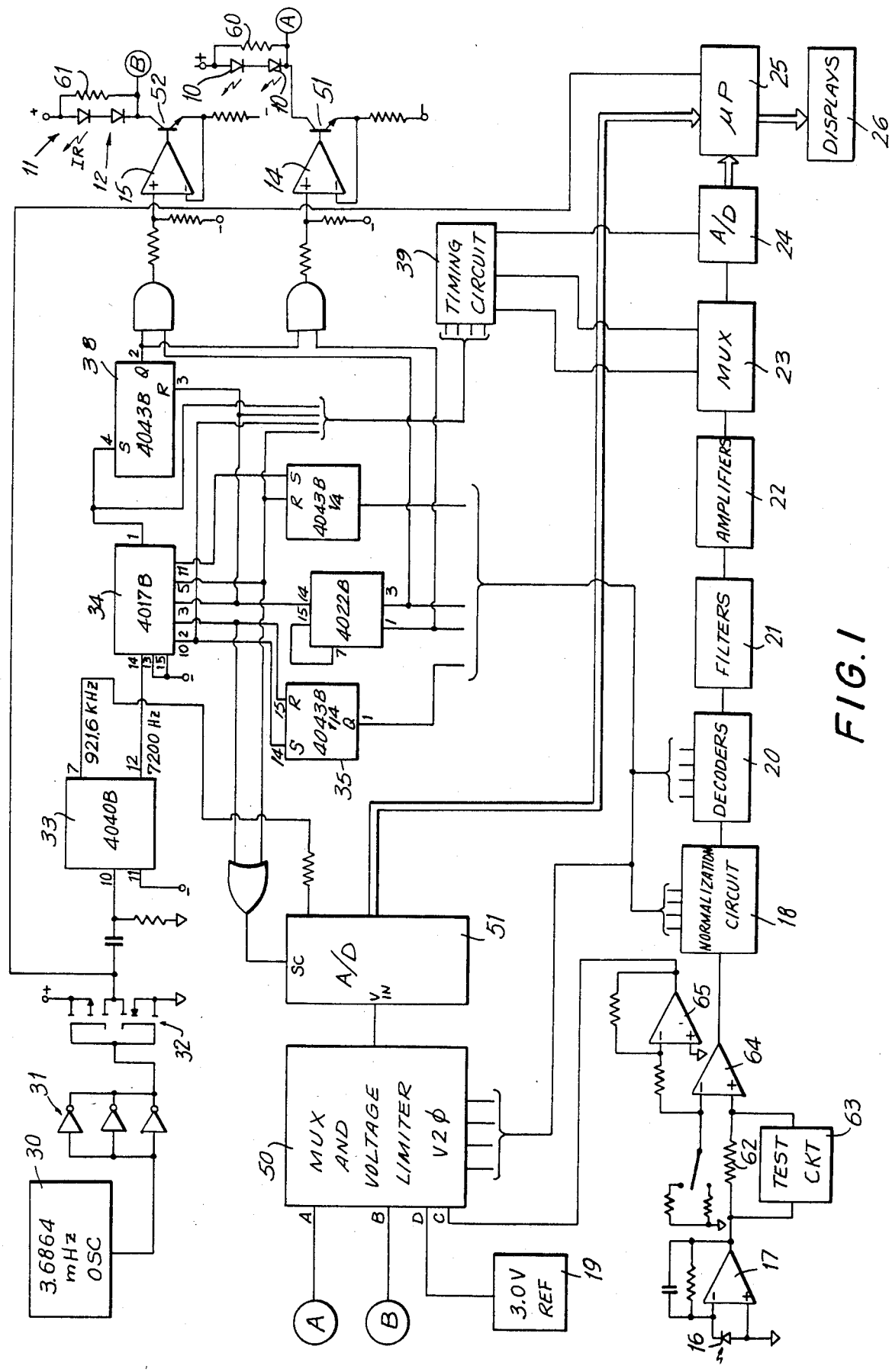
FIG. 1 is a block diagram of an oximeter incorporating the monitoring arrangement of the invention.

The oximeter is comprised of a pair of light sources of different wavelengths, in the form of a pair of LED's 10 emitting, for example, red light, and LED 11 emitting, for example, infrared radiation. The two red LED's 10 are connected in series, in a practical embodiment of the oximeter, in order to provide red radiation of sufficient intensity. A non-light emitting diode 12 may be connected in series with the infrared emitting diode 11, for purposes that will be dislosed in greater detail in the following disclosure. The red and infrared LED's are sequentially pulsed in a timing circuit to be more fully discussed, by way of amplifiers 14 and 15 respectively.

Radiation from the red and infrared diodes is sensed in a photodiode 16, after passing through the tissue, the output of the diode being applied to a current to voltage converter 17. The output of the current to voltage converter 17 is applied to Resistor 62 and test circuit 63 which can modulate incoming signals to verify overall circuit function. After 63 the signal is applied to variable gain amplifier 64 and then to normalization circuit 18 which serves the function, among others, of normalizing the signals with respect to a reference source 19. The normalized output of the circuit 18 is decoded in decoders 20, filtered in filters 21, amplified in amplifiers 22 and multiplexed in multiplexer 23. The decoders, filters and amplifiers constitute a pair of channels for processing the red and infrared radiation signals separately, and hence timing signals for properly processing the signals in the respective channels are obtained from the timing circuits, for controlling the normalization circuits, decoders and multiplexer. The output of the multiplexer 23 is converted to digital form in the analog to digital converter 24, for processing in accordance with the applicable algorithm in the microprocessor 25, to energize a display 26 for displaying the desired blood constituents. The analog to digital converter 24 and microprocessor 25 are of course also synchronized by the timing circuit.

The timing circuit, as may comprise a 3.6864 MHz oscillator 30, the output thereof being buffered by devices 31 and 32. The output of buffer 32 is then input to divider 33 such as CMOS type 4040B. One output of 33, at 921.6 KHz is the clock for A/D converter 41. Another output of 33, at 7200 Hz is the input to another divider 34. The outputs of 34, CMOS type 4017B are used with Flip-Flops 35, 36, 37 and 38 to generate timing signals for the system. Various outputs of 34, 35, 36, 37 and 38 are also used to synchronize multiplexer 23 and A/D converter 24 via additional timing circuitry 39.

THE MONITOR SYSTEM

In accordance with the invention, the following 4 system signals are applied to a multiplexer and voltage limiter circuit 50;

1. The voltage across the series connection of the two red LED's 10. This voltage may be derived therefore at the collector of the transistor driver 51 for these light emitting diodes. When the red LED's are not energized, the voltage at the collector of transistor 51 shoiuld be 5 volts (the positive supply source voltage). Sincer a typical voltage drop of 1.65 volts is expected across each of these LED's when energized, a voltage of approximately 1.7 volts should appear at the input A of the multiplexer when the red LED's are properly energized.

2. The voltage drop across the infrared LED 11. This voltage is derived at the collector of a transistor 52 that drives the infrared LED. In one embodiment of the oximeter of the invention, the oximeter may be selectively adapted for use at an individual's earlobe, or at an individuals finger. In order to enable the instrument to determine the instant application of the oximeter, so that it can be properly calibrated, the series diodes 12 may be connected in series with the infrared LED when the oximeter is to be employed for determining blood constituents in a finger, the conventional diode 12 being omitted when the oximeter is setup to determine blood constituents in an earlobe. Since the voltage drop expected across an energized infrared LED is about 1.3 volts and the expected voltage drop across the diode 12 is about 0.6 volts, it is apparent that the voltage at the input B of the multiplexer 50 will be 5 volts when the LED is not energized, 3.1 volts when the LED is properly energized and the oximeter is setup for measuring constituents of a finger and 3.7 volts if the infrared LED is properly energized and the oximeter is setup to measure blood constitents in an earlobe.

3. The output of the photodetector 16. This voltage may be obtained at the output of the inverting amplifier 65 and applied to an input C of the multiplexer 50.

4. The reference voltage of the source 19, which is connected to the input D of the multiplexer 50.

The output of the multiplexer 50 is applied to an analog to digital converter 41, the digital output thereof being applied to a microprocessor 25 for driving a display 26.

Suitable timing signals are applied, from the timing circuit, to the multiplexer 50, analog to digital converter 41 and microprocessor 25. Thus, it is necessary that the voltages across the LED's, and the output of the photodiodes 16 be multiplexed to the analog to digital converter 51 at times that the signals are valid. The signal across the LED's and photodiode are not valid upon initial energization, and hence, for example, the synchronization signals applied to the decoders 20 are all indicative of the valid state of the signals, and may be employed for synchronizing the multiplexer 50. The input D of the multiplexer 50 is of course valid at all times, and may be sampled at any desired time.

The analog to digital converter 51 may of course be synchronized with the signals that synchronize the analog to digital converter 24.

In the monitoring of the red and infrared LED's, there are four points in time that are of interest in determining possible probe and probe drive failures, i.e., the interval during which the red LED should be lit, the two intervals when the both LED's should be off, and the interval when the infrared LED should be lit. If the voltages measured at the monitor points are not within determined tolerances of the above discussed levels, the resultant digital signal applied to the microprocessor will result in the display of an error on the display device 26. Such errors may occur, for example, if the probe has been disconnected from the oximeter system. In this case the voltage measured at the LED's will be zero when the LED's should be on, and 5.0 volts when the LED's should be off (due to the use of the illustrated resistors 60, 61 respectively in parallel with the red and infrared LED's.) If this condition occurs, "No Probe" message may be displayed on the display device 26.

If, on the other hand, the red LED is open circuited, the voltage measured when the red LED should be on will be zero, and the other voltages monitored will be correct. In this case, for example, the error message and the ranges that the monitor voltages fall within may be displayed. Such displays enable the simple analysis of the fault.

If the voltage at the photodiode detector amplifier is less than 80 millivolts for an ear probe or less than 30 millivolts for a finger probe, a "Probe Lo" message may be displayed, indicating that an insufficient amount of either red or infrared light is being passed through the sample tissue. If the detector amplifier voltage is greater than 1.6 volts, a "Probe Off" message may be displayed, to indicate that the red or infrared light is probably not being passed through any tissue.

With respect to the reference voltage from the source 19, if this voltage is less than 2.9 volts or greater than 3.1 volts the proper normalization of the oximeter circuits will not occur, and hence an error message, such as "err 999" may be displayed.

In the flow diagram of FIGS. 2A–2F, the data structure LTTAB indicates samples taken during LED "on" times, as follows:

0 = 3.0 volt source
1 = infrared LED driver sample
2 = red LED driver sample
3 = photodetector sample during dark time
4 = photodetector sample during infrared time
5 = photodetector sample during red time.

The data structure DKTAB refers to samples taken before LED on times, as follows:

0 = 3.0 volts
1 = infrared LED driver sample
2 = red LED driver sample.

Figure 2A:
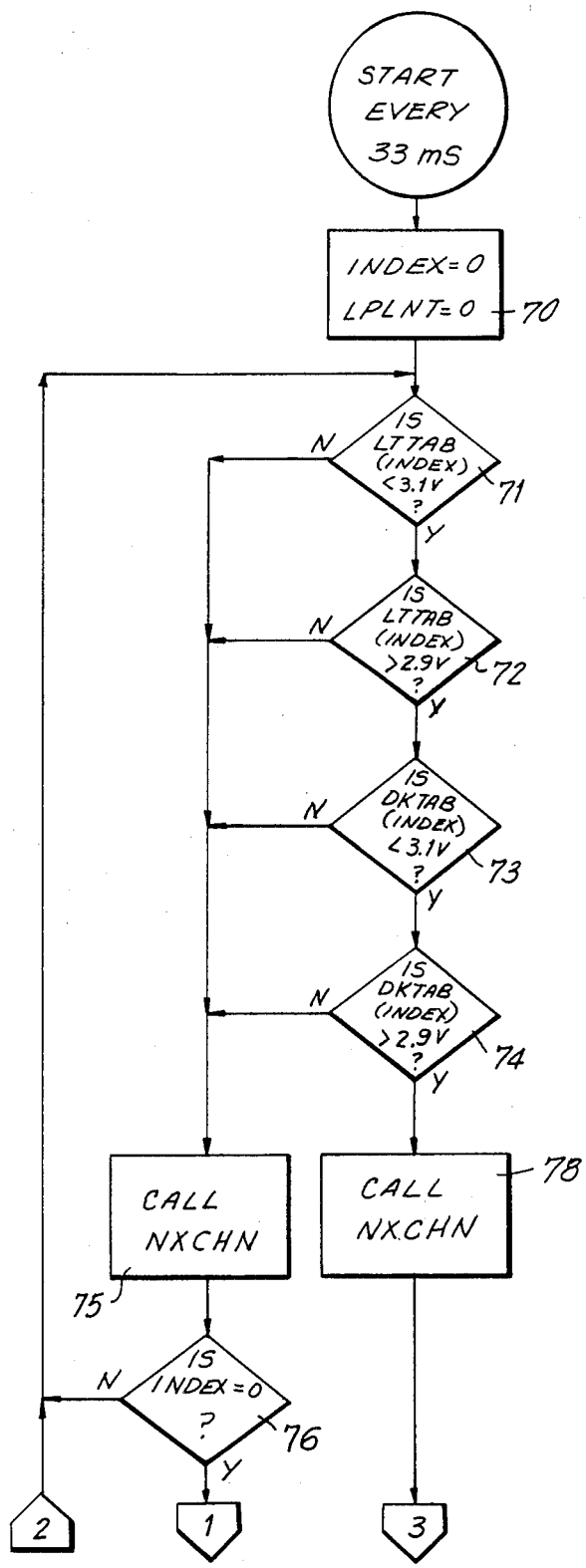

FIG. 2A shows the starting procedure for each monitoring cycle, which may occur under synchronization from the timing circuit at about 33 millisecond intervals.

In block 70, an index count and an error count LPCNT are set to zero. In blocks 71–74 the three volt source is tested during the LED on times and LED off times, and if the voltage is out of range, the index stepping subroutine NXCHN of FIG. 2B is called at block 75. If the index setting is zero, at block 76, the subroutine of FIG. 2C is called to step the error count LPCNT. In the event of continuous errors detected in the three volt source, the circuit loops continuously until the value of LPCNT is equal to at least 255, whereupon the program at block 77 of FIG. 2C calls an endless loop display of "err 999". These routines thereby enable a stabilization period for the three volt source, upon initially turning on the oximeter, so that an error is not called until a reasonable time has passed for the voltage level to become stable.

If the three volt source is within the proper range, the program of FIG. 2A calls the index stepping subroutine at block 78, and then jumps to the subroutine that commences at FIG. 2B. In block 80, the program jumps to the subroutine of FIG. 2E to set a value for the variable A, corresponding to the voltage across the infrared LED circuit, during LED on time. Thus, in FIG. 2E, the value of RNGFND, and hence the value of the variable A, is determined on the basis of voltage value thereof, with the variable A being set to an integer from 0 to 5. Similarly, in block 81 the subroutine of FIG. 2E is called to set a RNGFND value for the variable B corresponding to the detected voltage at the infrared LED circuit during off time. The variable C is set in block 82 to correspond to the output of the amplifier 17 durig infrared LED on times. The variable D is set in block 83, with a jump to RNGFND, to correspond to the voltage of the red LED's during red LED on time, and the variable E is similarly set in block 85 to correspond to the voltage of the red LED's during red LED off time. The variable F is set in block 86 to correspond to the output of the amplifier 17 during on times of the red LED's. Upon setting such values, the program jumps to the routione of FIG. 2F.

Figure 2F:
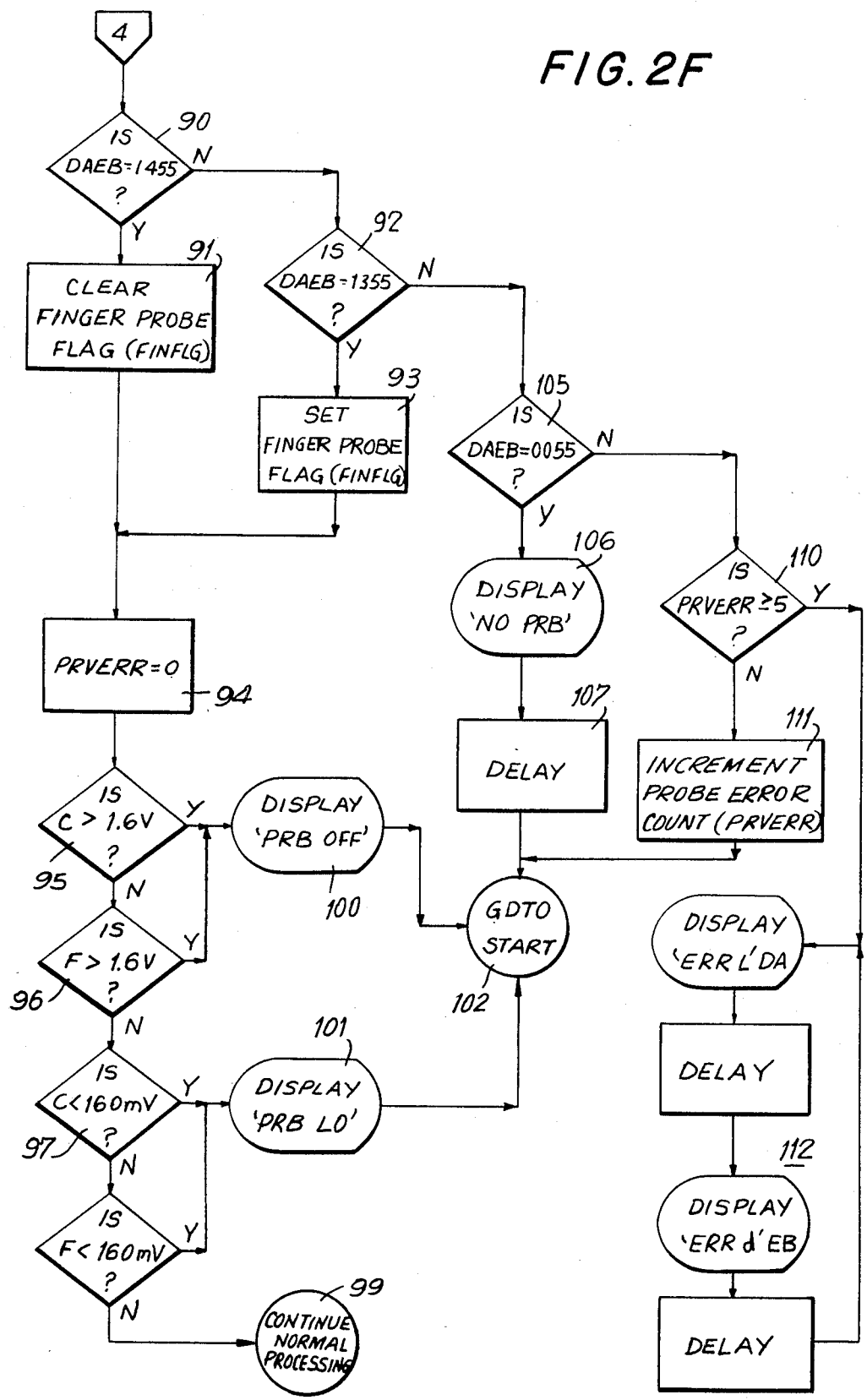

Referring to FIG. 2F, in block 90 the value DAEB is compared with the number 1455. This variable DAEB is a numerical string formed of the determined range values of the variables D, A, E and B respectively, in that order. If the value of DAEB is equal to 1455, as tested in block 90, then an ear probe must be provided in this system, and the finger probe flag is hence cleared in block 91. This serves to advise the oximeter of the fact that an ear probe is being employed and that the parameters employed in the algorithm must be set in accordance with ear probe measurements. On the other hand, if the value of DAEB is not equal to 1455, it is tested in block 92 to see if the value is 1355 thereby indicating the present of a finger probe. If a finger probe is indicated, block 93 ensures the setting of the finger probe flag to advise the oximeter of the use of the figure probe. An error count PRVERR is set to zero in block 94, followed by the testing in blocks 95-98 for out-of-range values of the variables C and F. If these values are within range, the program exits in block 99, to enable the oximeter to make the necessary calculations. If the values of C and F are incorrect, error displays are given at blocks 100 or 101 and the program jumps to the restart of the routine of FIG. A, from block 102.

If it was found in block 92, that the value of DAEB was not equal to 1355, it is evident that an error has been detected. In block 105 a test is made to determine if the value of DAEB is 0055. In this case, an indication of the absence of the probe is given in block 106, and, after a suitable delay in block 107 to enable the connection of a probe, the program returns to the start from block 102.

For other values of DAEB, a determination is made in block 110 of the number of such errors, and if the number is less than 5, the error count PRVERR is incremented in block 111 to return to the start of the program at block 102. If, on the other hand, the number of detected errors is equal to or greater than 5, a suitable delay and display endless loop 112 advises the user of such errors.

While the invention has been disclosed and described with reference to a single embodiment, it will be apparent that variations and modifications may be made therein, and it is therefore intended in the following claims to cover each such variation and modification as falls within the true spirit and scope of the invention.

We claim:

1. In a monitor system for an oximeter wherein at least two light emitting devices of different wavelengths are alternately energized, the light therefrom being received by a light detector for application to a processing circuit for determining the constituents of a tissue between said light emitting device and light detector, the oximeter including timing means for controlling the light emitting devices, to have different on times and off times and to control the light detector and processing circuits; the improvement wherein said monitor system comprises means responsive to said timing means for separately sensing the voltages of said light emitting devices and the output of said light detector during the absence of energization of said light emitting devices and also during the energization of said light emitting devices to provide a plurality of test values, and data processor means responsive to said test values for indicating the occurrence of any of said test values outside of a determined range corresponding to the respective test value, means enabling the insertion of resistance means in series with one of said light emitting devices as a function of the type of tissue to be measured, and means responsive to the sensed value of said one light emitting devices during its energized time for enabling the setup of the system to make measurements in that type of tissue.

2. The monitor system of claim 1 wherein said oximeter is further provided with a voltage reference source, and said sensing means is connectd to produce a test value responsive to the voltage of said reference source.

3. The monitor system of claim 1 wherein said light emitting devices are light emitting diodes.

4. The monitor system of claim 3 wherein said sensing means senses the voltages of said light emitting diodes at times following energization and deenergization thereof, at which time the voltages are valid.

5. The monitor system of claim 1 wherein said data processing means comprises a microprocessor, a display connected to be operated by said microprocessor, and an analog to digital converter for receiving said test values and applying them to said microprocessor.

6. The monitor system of claim 5 wherein said test values may selectively fall within any of a plurality of ranges of possible test values and said microprocessor comprises means for assigning integer range numbers to said test values as a function of the range within which the test values fall and testing a composite of said assigned range number to determine the operability of said oximeter.

7. A method for monitoring an oximeter wherein at least two light emitting devices of different wavelengths are alternately energized, the light therefrom being received by a light detector for application to a processing circuit for determining the constituents of a tissue between said light emitting devices and light detector, the oximeter including timing means for controlling said light emitting devices, light detector and processing circuit; said method comprising sensing the voltages across said light emitting devices to provide a plurality of first test values at signal valid times, assigning integer values to said test values, in accordance with their amplitude, to provide a plurality of range values, combining said range values, and testing said combined range values to indicate the operability of said oximeter.

8. The method of claim 7 wherein said step of combining comprises forming a string from said range values.

9. The method of claim 7 further comprising sensing the output of said light detector during the energization of said light emitting devices to provide further test values, and further comprising testing the values of said further test values following said step of testing said combined values, in order to indicate the operating conditions of said light detector.

* * * * *